United States Patent [19]

Conway et al.

[11] Patent Number: 5,176,666

[45] Date of Patent: Jan. 5, 1993

[54] EXTERNAL URINARY CATHETER HAVING INTEGRAL ADHESIVE MEANS

[75] Inventors: Anthony J. Conway; Philip J. Conway, both of Chatfield; Richard D. Fryar, Jr., Rochester, all of Minn.

[73] Assignee: Rochester Medical Corporation, Stewartville, Minn.

[21] Appl. No.: 876,702

[22] Filed: Apr. 29, 1992

Related U.S. Application Data

[63] Continuation of Ser. No. 611,193, Nov. 10, 1990, abandoned.

[51] Int. Cl.$^5$ ............ A61F 5/44; A61F 6/02; A61F 6/04; A61K 1/02
[52] U.S. Cl. .................. 604/349; 604/346; 604/347; 604/351; 128/842; 128/844; 427/2
[58] Field of Search ............... 604/346–347, 604/349, 351; 128/842, 844, 883, 885; 427/2

[56] References Cited

U.S. PATENT DOCUMENTS

| | | |
|---|---|---|
| Re. 33,206 | 5/1990 | Conway et al. ............ 604/349 |
| D. 299,865 | 2/1989 | Kamstrup-Larsen et al. . |
| 3,739,783 | 6/1973 | Broerman ............ 604/352 |
| 4,168,699 | 9/1979 | Hauser . |
| 4,187,851 | 2/1980 | Hauser . |
| 4,367,732 | 1/1983 | Poulsen et al. . |
| 4,378,018 | 3/1983 | Alexander et al. . |
| 4,475,910 | 10/1984 | Conway et al. . |
| 4,477,325 | 10/1984 | Osburn . |
| 4,534,768 | 8/1985 | Osburn et al. . |
| 4,540,409 | 9/1985 | Nystrom et al. . |
| 4,581,026 | 4/1986 | Schneider . |
| 4,586,974 | 5/1986 | Nystrom . |
| 4,589,874 | 5/1986 | Riedel et al. . |
| 4,626,250 | 5/1986 | Schneider . |
| 4,640,668 | 2/1987 | Hauser . |
| 4,699,616 | 10/1987 | Nowak et al. . |
| 4,759,753 | 7/1988 | Schneider et al. . |
| 4,769,099 | 9/1988 | Therriault . |
| 4,820,289 | 4/1989 | Coury et al. ............ 604/349 |
| 4,846,909 | 7/1989 | Klug . |
| 4,863,449 | 9/1989 | Therriault et al. . |
| 4,867,748 | 9/1989 | Samuelson . |
| 4,885,049 | 12/1989 | Johannesson . |
| 4,894,059 | 1/1990 | Larsen et al. . |
| 4,932,948 | 6/1990 | Kernes et al. . |

FOREIGN PATENT DOCUMENTS

| | | |
|---|---|---|
| 0390720 | 10/1990 | European Pat. Off. . |
| WO86/00816 | 2/1986 | PCT Int'l Appl. . |
| 2106784 | 4/1983 | United Kingdom . |

*Primary Examiner*—David J. Isabella
*Assistant Examiner*—A. Zuttarelli

[57] ABSTRACT

An external urinary catheter having integral adhesive means. The external urinary catheter includes (a) a single tubular sheath having a unitary construction made of silicone rubber, the silicone rubber having an inner surface and an outer surface; and (b) a layer of adhesive material bonded to a first portion of the inner surface; wherein the adhesive material can releasably contact portions of the outer surface such that the inner surface of the silicone rubber sheath can be rolled up on the outer surface thereof so that the adhesive layer on the first portion of the inner surface comes into releasable contact with the portions of the outer surface, and such that the adhesive material on the outer surface will then release any portions of the outer surface with which it has come into contact, while remaining bonded to the inner surface, when the silicone rubber sheath is forcibly unrolled. A method of making an external urinary catheter is also disclosed. Said method includes the steps of (a) coating a first portion of a mandrel with an adhesive material (b) subsequently overcoating the mandrel with a silicon rubber solution to form an overcoat layer made of unvulcanized silicone rubber; and (c) vulcanizing the unvulcanized silicon rubber such that constituents of the silicone rubber cross-link to form an elastomeric sheath having a unitary construction made of vulcanized silicone rubber; the silicone rubber sheath having an inner surface and out outer surface; and the adhesive material being bonded to a first portion of the inner surface.

10 Claims, 5 Drawing Sheets

U.S. Patent    Jan. 5, 1993    Sheet 1 of 5    5,176,666
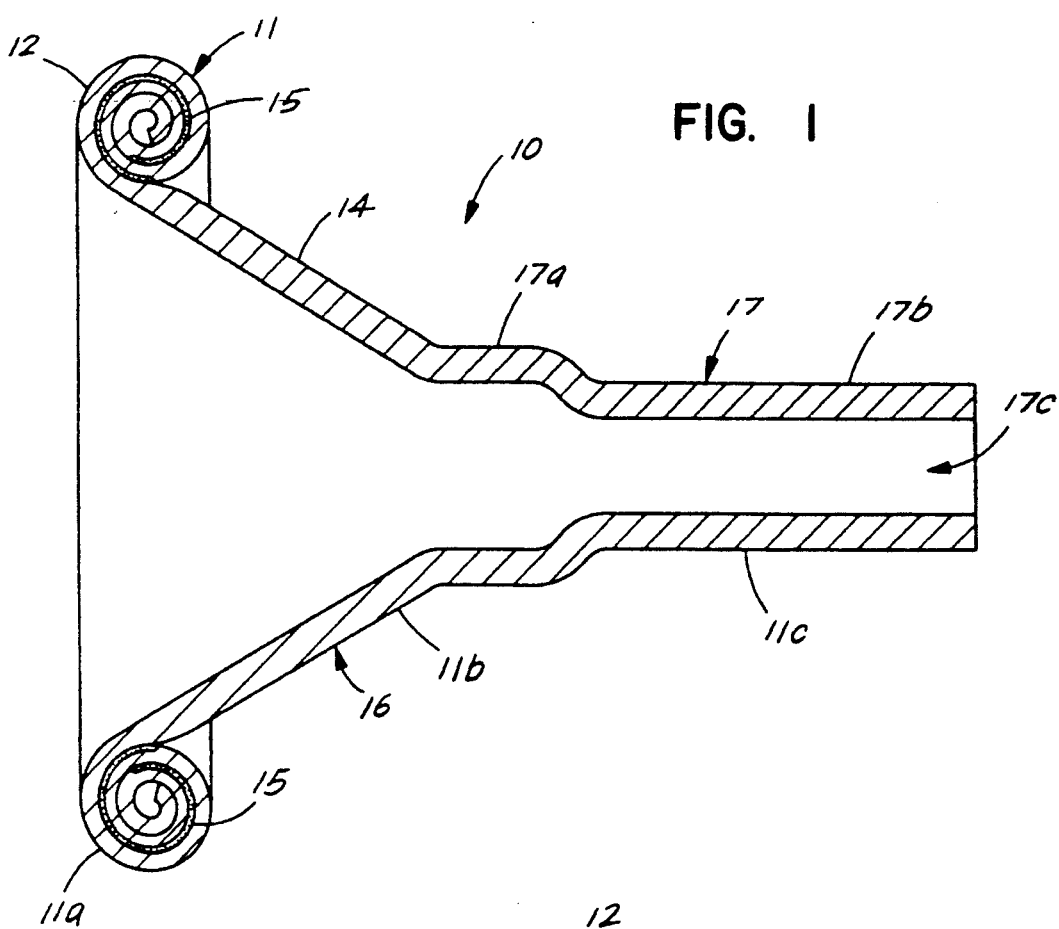
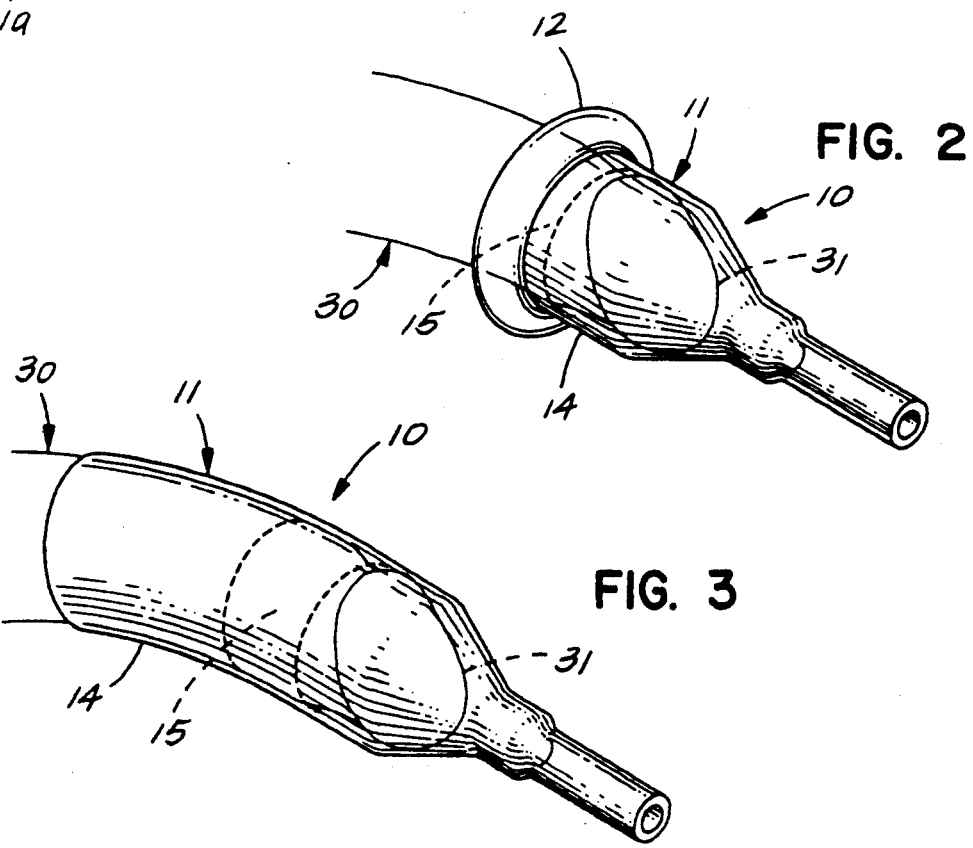

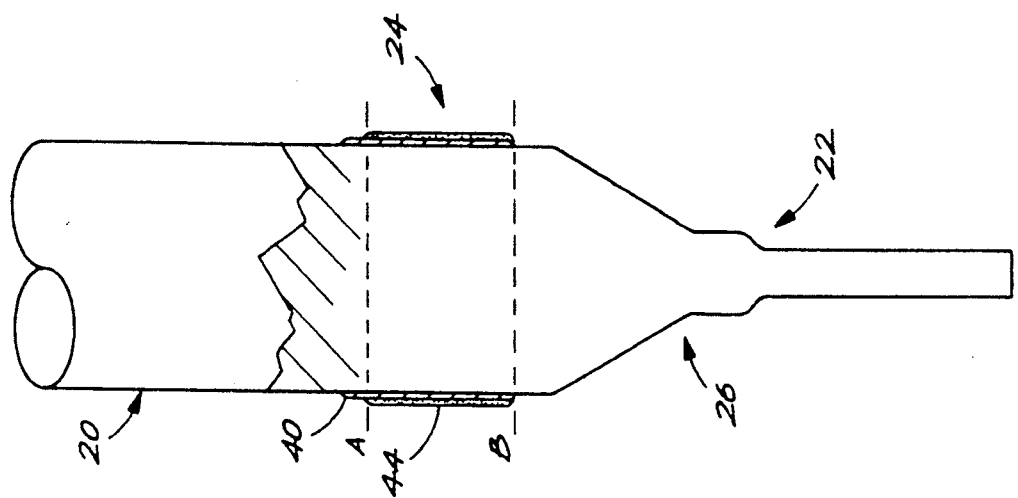
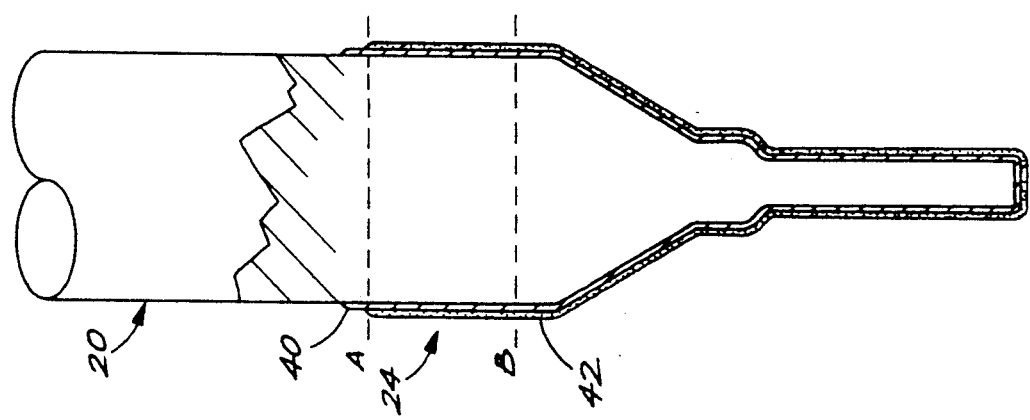
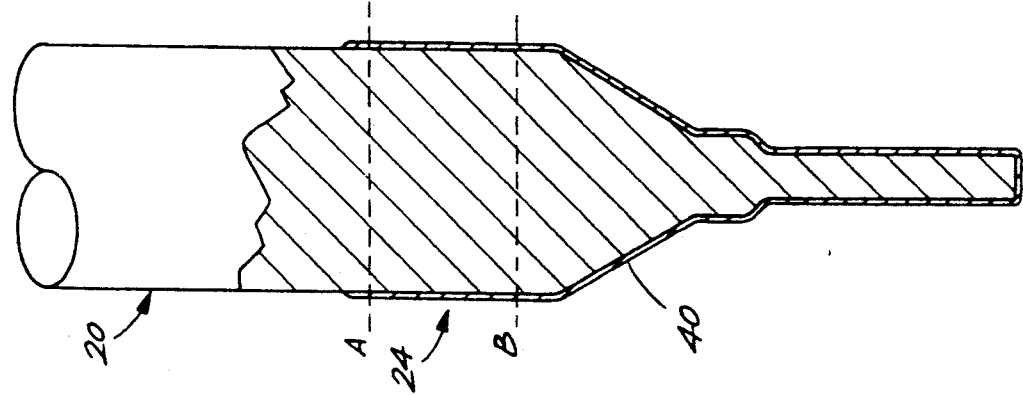
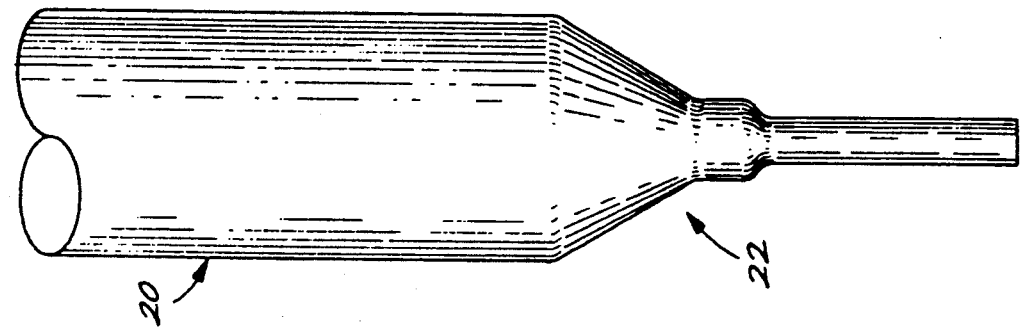

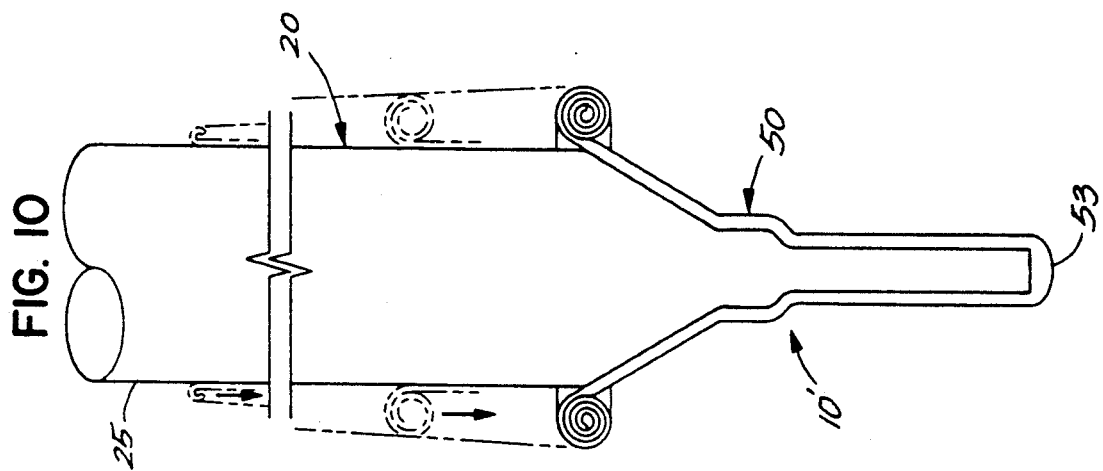
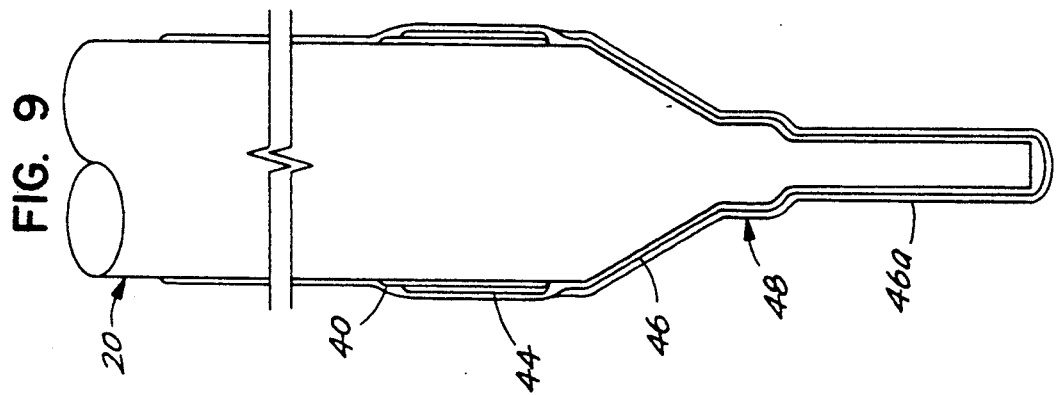
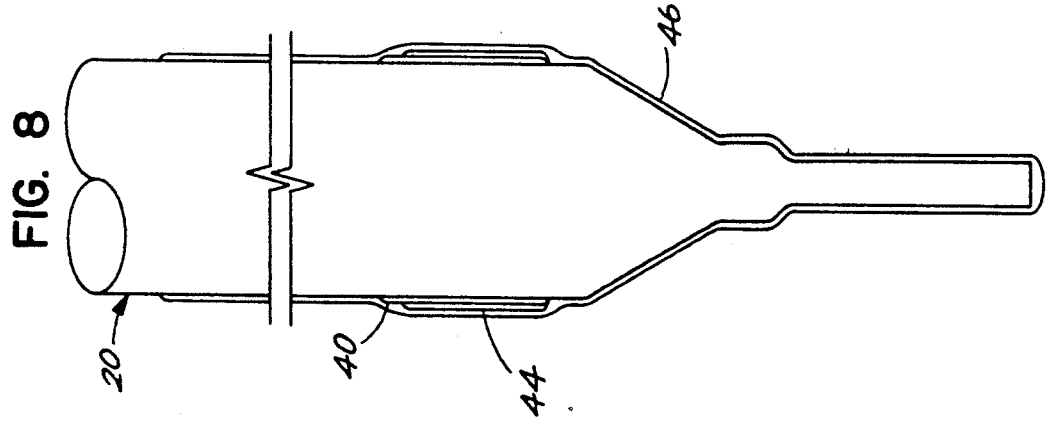

EXTERNAL URINARY CATHETER HAVING INTEGRAL ADHESIVE MEANS

This is a continuation of application Ser. No. 07/611,193, filed Nov. 9, 1990, now abandoned.

Field of the Invention

The present invention relates to external urinary catheters or male condom catheters for channeling unrestrained urinary discharges into urine collection devices.

Background of the Invention

Prior to the issuance of the Conway et al. patent (U.S. Patent No. 4,475,910) (reexamined and reissued as U.S. Pat. No. RE 33,206 on May 1, 1990), external male urinary catheters or condom catheters were generally retained on a penis of an incontinent male with an adhesive tape of one type or another.

The adhesive coated catheter disclosed by Conway et al. provided incontinent males with a self-sealing external catheter which required no tapes, was easier to put on, and had functional advantages over prior art catheters, such as reduced leakage due to the improved seal between the catheter and the penis. The "strapless" catheter of Conway et al. has proven to be a great commercial success and has become the catheter of choice for many men who are incontinent and must wear an external urinary catheter.

Similar strapless catheters have been disclosed in subsequent patents (e.g. U.S. Pat. Nos. 4,581,026; 4,863,449; 4,769,099; 4,846,909; and 4,885,049). Each of the aforementioned patents, including the Conway et al. patent, disclose external catheters which provide a construction having at least three distinct layers, namely an adhesive layer, an elastomeric sheath, and a release layer. In each case, the respective inventors have devised devices which insure that when the elastomeric sheath is "rolled up" in a pre-use storage orientation, the adhesive layer is sandwiched between an inner surface of the elastomeric sheath and an outer surface of the elastomeric sheath, with the release layer interposed between the adhesive layer and the outer surface.

The release layer has been critical to the aforementioned catheters because it is very important to enable the adhesive layer to separate from the outer surface of the elastomeric sheath when the condom catheter is unrolled onto the penis of the user. If the adhesive layer sticks to the outer surface of the elastomeric sheath when it is in the "rolled up" pre-use orientation, which it will if the sheath is made of latex, the catheter will be difficult to apply and unacceptable in the marketplace. Thus, the prior inventors have been very concerned with providing a release layer which will "release" the adhesive from the outer surface of the elastomeric sheath such that the adhesive layer remains bonded only to the inner surface of the sheath and is subsequently able to stick to the external surface of the penis so as to provide for effective retention of the catheter thereon. It will be appreciated that each of the aforementioned patents disclose the concept of laminating either the outer surface of the catheter or the exposed surface of the adhesive layer in order to provide for the release layer and to allow the catheter to work in the manner described above.

The Conway et al. patent discloses a catheter including an elastomeric sheath having a release layer on an outer surface thereof and an adhesive material sandwiched between the release layer and the inner surface of the elastomeric sheath when the inner surface is rolled up upon the outer surface and the release layer in the pre-use orientation.

Johannesson (U.S. Pat. No. 4,885,049) discloses a slightly different approach for providing a similar device. Schneider (U.S. Pat. No. 4,581,026) discloses two means of securing an external catheter to a penis. One requires the use of an adhesive pad or tape, and the other requires the use of an adhesive band on an inner surface of the sheath which will not bond to an outer surface thereof because the outer surface is coated with a "suitable elastomeric agent" such as silicone rubber.

Riedel et al. (U.S. Pat. No. 4,589,874) also disclose a catheter having an adhesive on an inner surface of an elastomeric sheath which is in contact with release material on the outer surface of the elastomeric sheath. The adhesive is released from a release material when the catheter is unrolled onto a penis. Schneider (U.S. Pat. No. 4,676,250) and Klug et al. (U.S. Pat. No. 4,846,909) also disclose similar adhesive means.

It will be appreciated from a detailed review of the aforementioned patents, that constructing these "layered" catheters can be quite difficult. Each requires means for constructing a catheter including three "layers". These three layers are the adhesive layer, the elastomeric sheath, and the release layer which allows the adhesive layer to be rolled up upon the outer surface of the elastomeric sheath such that the release layer is interposed between the adhesive layer and the outer surface thereof, thus enabling a user to easily unroll the elastomeric sheath onto the user's penis without undo difficulty resulting from substantial adhesion between the adhesive layer and the outer surface.

In actual practice, it is believed that each of the aforementioned inventions have an elastomeric sheath made of a latex material. The adhesive layer is generally a band of pressure sensitive adhesive, and the release layer generally consists of silicone rubber, to which the pressure sensitive adhesive will not bond. The prior art catheters each function because the adhesive will bond to the latex sheath, but will not bond to the silicone rubber release layer. Thus, when the catheter is rolled up into the pre-use orientation, each of the aforementioned prior art catheters consist of a latex sheath, coated on the outside with a silicone rubber "release" layer, with a band of adhesive material sandwiched between an inner latex surface, to which the adhesive is bound, and an outer silicone rubber surface interposed between the outer latex surface and the adhesive material. When the catheter is unrolled, the adhesive will stick only to the latex surface while releasing from the silicone rubber surface.

In addition to being fairly difficult to manufacture, these multi-laminated catheters have a number of important drawbacks. One of the most important drawbacks is the fact that latex materials contain leachable chemical constituents which can cause a wide range of skin reactions. This problem is especially accentuated in aqueous environments, often created with the presence of urine. It will be appreciated that latex catheters will absorb aqueous fluids such as urine and become wetted, thereby enhancing the opportunity for leachates to irritate the user's skin. Because many patients have to wear these catheters continuously, the risk of irritating the skin is quite significant.

Leachates found in latex may also "bloom" on the surface of the adhesive material when the catheter is in storage, thus weakening the adhesive bond which might otherwise be possible between the catheter and the penis when the catheter is applied thereto.

The aforementioned urinary catheters also have other significant problems, such as delamination of the release layer and the elastomeric sheath during storage; the unattractive "old rubber" smell characteristic of latex products which have been stored for a significant period of time; the resistance to the passage of light through the latex sheath which limits ones ability to view the condition of the penis through the opaque latex sheath; and the use of powders on the surface of the latex sheath which tend to interfere with the adhesion between the adhesive layer and the penis.

It will be appreciated, therefore, that there are significant problems with the prior art external catheters and the methods for making the same. The present invention provides advantages over the prior art catheters and over the prior art methods for manufacturing such catheters, and also offers other advantages over the prior art and solves other problems associated therewith.

Summary of the Invention

Accordingly, it is an object of the present invention to provide an improved, external urinary catheter having adhesive means and a cost effective method of making such catheters. It is a further object of the present invention to provide an external urinary catheter having a unitary construction which offers significant advantages over the prior art catheters. In accordance with the present invention, an external urinary catheter is provided, comprising a single tubular sheath having a unitary construction made of silicone rubber, said silicone rubber sheath having an inner surface and an outer surface; and further comprising a layer of adhesive material integrally bonded to a first portion of the inner surface; wherein the adhesive material can releasably contact portions of the outer surface such that the inner surface of said silicone rubber sheath can be rolled up upon the outer surface thereof so that the adhesive layer on the first portion of the inner surface comes into releasable contact with portions of the outer surface, and such that the adhesive material on the inner surface will then release the portions of the outer surface, with which it has come into releasable contact, while remaining bonded to the inner surface, when said silicone rubber sheath is forcibly unrolled. In preferred embodiments, the portion of the inner surface to which the adhesive material is bonded is a tubular strip forming a continuous band on an inside of the silicone rubber sheath. The adhesive material is preferably a synthetic material which bonds to silicone rubber when in contact with unvulcanized silicone rubber during a vulcanizing process such that the adhesive material cannot be peeled away or otherwise separated from the vulcanized silicone rubber surface in an even layer. Preferably the adhesive material is an acrylic adhesive which can be bonded to silicone rubber during a vulcanizing process or as a result thereof. The preferred external urinary catheter includes a single tubular sheath having a unitary construction made of silicone rubber and a layer of adhesive material integrally bonded to a first portion of an inner surface thereof, wherein the inner surface of the silicone rubber sheath is rolled up on the outer surface thereof for storage of the catheter prior to use such that the adhesive material is in releasable contact with portions of the outer surface, and wherein the adhesive material on the inner surface will release any portion of the outer surface with which it is in contact when the silicone rubber sheath is forcibly unrolled.

The present invention also includes a method of making an external urinary catheter comprising the steps of coating a first portion of a mandrel with an adhesive material; subsequently overcoating the mandrel with a silicone rubber solution to form an overcoat layer of unvulcanized silicone rubber; and vulcanizing the unvulcanized silicone rubber such that constituents of the silicone rubber cross-link to form an elastomeric sheath having a unitary construction made of vulcanized silicone rubber, wherein the silicone rubber sheath has an inner surface and an outer surface and wherein the adhesive material is preferably integrally bonded to a first portion of the inner surface. In preferred embodiments, the mandrel is generally cylindrical and can be made, either partially or completely of tetrafluoroethylene (Teflon ®) and the step of coating a first portion the mandrel with adhesive material is preceded by coating the mandrel with a mandrel release agent, preferably polydimethylsiloxane, and followed by a step of dipping the mandrel in a solvent fluid to strip any adhesive material from a second portion of the mandrel. The solvent fluid will preferably be an organic solvent such as xylene, toluene, trichlorethane and the like. In preferred embodiments the silicone rubber solution will contain the solvent hexamethyldisiloxane and the step of overcoating the mandrel will include dipping the mandrel in a silicone rubber solution containing hexamethyldisiloxane. The present invention also includes an external urinary catheter made in accordance with the aforementioned method.

It will be appreciated that the present invention offers many advantages over the prior art methods and the prior art catheters. The present methods provide numerous advantages over the prior art methods including simplicity, cost savings and an end product which is significantly more marketable than the prior art catheters. The external urinary catheter of the present invention has a unitary construction which will not delaminate and which is made of superior materials which are less likely to cause skin irritation and the like. The silicone rubber may also be more translucent than the opaque latex devices, so that the condition of the penis inside the catheter may be easily observed without removing the catheter.

It will be appreciated that the present applicants have devised a way to eliminate the need for including a release layer on the outer surface of the elastomeric sheath of the catheter. Instead, the present inventors have made the elastomeric sheath of silicone rubber which, once formed, does not bind to the adhesive material bound to the inner surface of the elastomeric sheath. While an uninformed observer might consider this to be rather straightforward prior to consultation with those of skill in the art, it will be appreciated that those of skill in the art of making external male catheters having an adhesive layer on the inside surface of an elastomeric sheath, were unaware of methods of securing the adhesive material to silicone rubber while providing for a substantial lack of adhesion between the same adhesive layer and the outer surface of the silicone rubber sheath. The applicants have provided a solution to this dilemma and have, in the process, provided users of external urinary catheters with a far superior catheter made of superior materials which reduce the risk of skin irritation and infection.

When the present invention is rolled up in the pre-use orientation, the adhesive material is bonded to the inner surface of the homogeneous silicone rubber sheath and in contact with the outer surface of the silicone rubber sheath. When unrolled over the penis, the adhesive material releases from the outer surface of the silicone rubber sheath because of the nature of the silicone rubber surface and the lack of adhesion between the adhesive material and such a surface. However, the adhesive material remains firmly bonded to the inner surface of the silicone rubber sheath and is then in position to adhere to the outer surface of the penis so as to secure the external catheter thereto. In preferred embodiments, the elastomeric catheter sheath is made entirely out of medical grade silicone rubber. The adhesive is preferably a medical grade acrylic adhesive, which under normal circumstances, will not bond to silicone rubber. For this reason, the adhesion between the adhesive material and the outer surface of the silicone rubber catheter sheath will be minimized when the sheath is unrolled during application by the user.

The urinary catheter of the present invention is far superior to the prior art catheters presently on the market. The process of vulcanizing the silicone rubber elastomer while in contact with the adhesive material eliminates the need for the latex layer between the adhesive and a silicone rubber release layer on the outer surface of the elastomeric sheath. Instead, the elastomeric sheath is made of pure silicone rubber which has no leachates or extractives, it is non-allergenic, non-wetting and odorless, and can be totally transparent. Furthermore, the bond between the adhesive and the silicone rubber is cross-linked.

In addition, by eliminating the complex manufacturing techniques required for the prior art multi-laminated catheters, it is possible to produce the silicone rubber catheter for the same cost as the laminated latex catheters which are made of less desirable materials.

The applicants wish to note that the following terms have the respective meanings set forth hereinbelow. "Silicone rubber" means any silicone rubber including, but not limited to, fluoro silicone rubber and the like. A "silicone rubber solution" is an uncatalyzed or unvulcanized fluid containing silicone rubber and other constituents which can be cross-linked to form vulcanized silicone rubber during a vulcanizing process. It is not necessarily a solution per se, but may be an emulsion, a dispersion or any other fluid which can effectively carry such unvulcanized constituents in a generally homogeneous system when well mixed. "Integrally bonded" means having constituents in each of two different polymeric compounds at issue which are at least partially cross-linked with one another such that one compound cannot be evenly separated from the other compound along an even surface separating the two compounds. A "vulcanizing process" is a process of cross-linking constituents of a polymer, copolymer or other elastomer, or constituents of two adjacent compounds of this general kind. To "vulcanize" is to cross-link segments of polymer chains to strengthen the polymer and to permit it to be more resilient. "Unvulcanized" means a state wherein there is substantially less cross-linking between constituents of compounds used to form a final product during an anticipated vulcanization process.

These and various other advantages and features of novelty which characterize the present invention are pointed out with particularity in the claims annexed hereto and forming a part hereof. However, for a better understanding of the present invention, its advantages, and other objects obtained by its use, reference should be made to the drawings which for a further part hereof, and to the accompanying descriptive matter, in which preferred embodiments of the present invention are illustrated and described.

Brief Description of the Drawings

In drawings, in which like reference numerals indicate corresponding parts of the preferred embodiment of the present invention throughout the several views, FIG. 1 is an enlarged sectional view of an external unit urinary catheter of the present invention shown in its pre-use or orientation;

FIG. 2 is a perspective view of the external urinary catheter shown in FIG. 1 when it is partially unrolled onto a penis;

FIG. 3 is a perspective view of the external urinary catheter shown in FIG. 2 when the catheter is fully unrolled onto the penis;

FIG. 4 is a side view of a mandrel used to form the external urinary catheter of the present invention;

FIG. 5 is a partial cross-sectional view of the mandrel shown in FIG. 4 when partially coated with a silicone fluid;

FIG. 6 is a view similar to FIG. 5 after the mandrel is partially coated with adhesive material;

FIG. 7 is a view similar to FIG. 6, after a portion of the silicone fluid and the adhesive material on the mandrel have been stripped away;

FIG. 8 is a view similar to FIG. 7 after an overcoat layer of silicone rubber solution has been coated on the mandrel over the adhesive material and silicone fluid remaining on the mandrel in FIG. 7 following the step of stripping a portion of the adhesive material and silicone fluid away;

FIG. 9 is a view similar to FIG. 8 following the application of a second coating of a silicone rubber solution to a portion of the mandrel shown in FIG. 8 following the application of the initial overcoat layer;

FIG. 10 is a view similar to FIG. 9 following the curing or vulcanizing of the external urinary catheter showing the rolling up of an upper portion of a silicone rubber sheath portion of the external urinary catheter of the present invention in phantom and the pre-use orientation of the external urinary catheter prior to removing the catheter from the mandrel and separating an enclosed tip from the lower end of the catheter;

Detailed Description of the Preferred Embodiments

Figure 12:
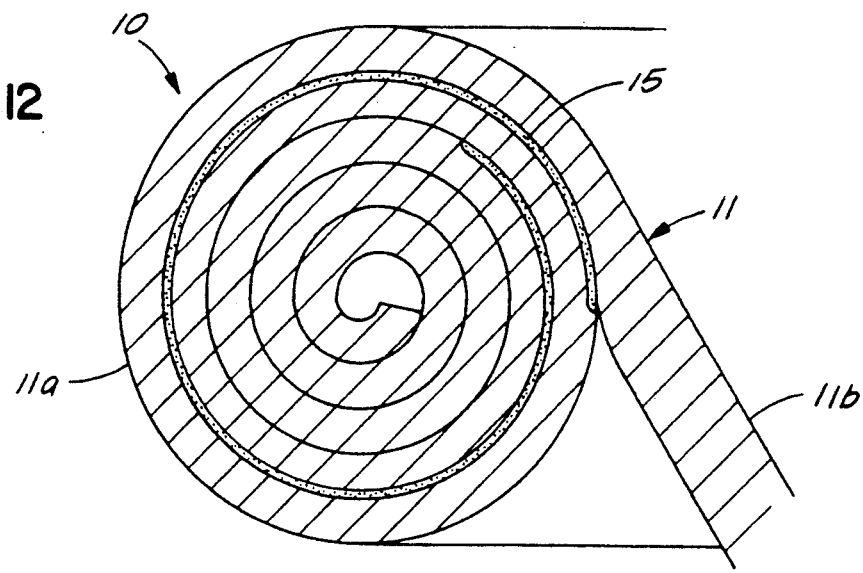
FIG. 12 is an enlarged cross-sectional view of a portion of the external urinary catheter shown in FIG. 1 and its pre-use orientation.
Figure 11:
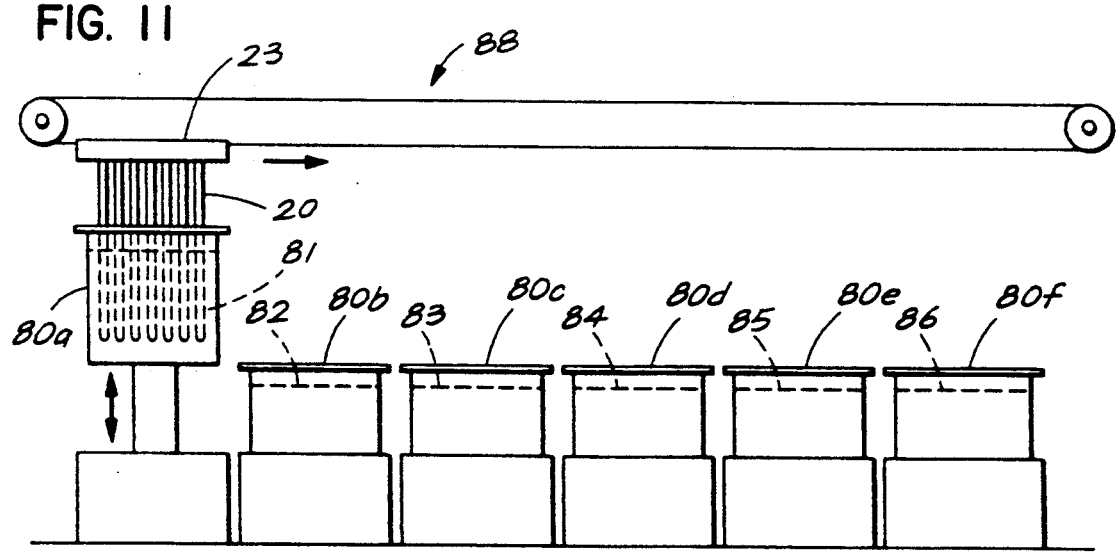
FIG. 11 is a schematic illustration of the mechanized system used to coat the mandrels shown in FIGS. 4–10.

Referring now to the drawings, and specifically to FIGS. 1, 2 and 3, the external urinary catheter 10 of the present invention includes a single tubular sheath 11 having a unitary construction made of silicone rubber. The silicone rubber sheath 11 has an inner surface 12 and an outer surface 14. Following manufacture and during pre-use storage the external catheter 10 will generally have a pre-use orientation shown in FIG. 1 wherein an upper portion 11a is rolled up upon itself as shown in FIG. 1 so that the inner surface 12 is rolled up against and comes into contact with the outer surface 14. Interposed between a portion of the inner surface 12 and the outer surface 14 when the tubular sheath 11 is rolled up on itself and the external catheter is in the pre-use orientation, is an adhesive layer 15 which is bonded to a portion of the inner surface 12. Although the adhesive layer 15 adheres to the inner surface 12 it does not adhere to the outer surface 14 when the upper portion 11a of the silicone rubber sheath 11 is unrolled. As discussed further hereinbelow, the adhesive material 44 (see FIGS. 6–9), which makes the adhesive layer 15 is bonded to the inner surface 12 by a catalyzed process, preferably a vulcanizing process, in which constituents within the adhesive material are cross-linked to constituents within the silicone rubber sheath 11 which is formed from an unvulcanized silicone rubber solution overcoat layer 46 (see FIGS. 8 and 9) during the vulcanizing process. Once the adhesive material 44 is bonded to the inner surface 12 of the silicone rubber sheath 11 to form the adhesive layer 15 during the vulcanizing process, and the remaining surfaces of the silicone rubber catheter 10 are formed to this process, the adhesive layer 15 will no longer irreversibly adhere to any of the remaining surfaces of the silicone rubber sheath 11. Although the adhesive will releasably adhere or stick to such surfaces, when a moderate force is used to separate the adhesive layer 15 from such surfaces, other than the surface to which it is bonded, it will result in the separation of the adhesive layer 15 from those surfaces. Therefore, the contact which will generally occur between the adhesive layer 15 and these other surfaces will be referred to herein as "releasable contact" or "releasable adherence". This type of contact or adherence is characterized in that it permits a relatively easy separation of the adhesive layer 15 from any of the silicone rubber surfaces of the sheath 11 to which it adheres or contacts in such a manner.

The external urinary catheter 10 also includes a conical tip 16 made up of a conical portion 11b of the tubular sheath 11, and a tube 17 having an enlarged portion 17a interposed between the conical tip 16 and a narrowed portion 17b. The tube 17 is made up of a lower tubular portion 11c of the tubular silicone rubber sheath 11 which is interconnected with the upper portion 11a of the sheath 11 by the conical portion 11b. At the distal end of the tube 17 is a urinary drainage tube junction opening 17c which is designed to communicate with a urinary drainage tube (not shown) to permit urine to pass through the tube 17 into the urinary drainage tube (not shown) for subsequent collection of the urine in a suitable collection device (not shown).

In order to use the external urinary catheter 10 of the present invention, a user, or perhaps a health care professional, will engage the tip 31 of a penis 30 within the conical portion 11b of the tubular sheath 11 when the catheter 10 is in the pre-use orientation shown in FIG. 1. The upper portion 11a of the tubular sheath 11 is then unrolled using moderate force to press the rolled up portion of the upper portion 11a away from the tip 31 of the penis 30. This can generally be accomplished by pressing on the rolled up portion of the upper portion 11a with one's thumb and forefinger (not shown). As the upper portion 11a is unrolled, the adhesive layer 15 will release the outer surface 14 so that the upper portion 11a is relatively easy to unroll onto the penis 30. As the adhesive layer 15 comes into contact with the outer surface of the penis 30, however, the adhesive layer will adhere to the penis 30 so as to secure the catheter 10 to the penis 10. Preferably, the adhesive layer 15 will provide a seal which secures the tubular sheath 11 to the penis 30 and prevents leakage of urine past the area where the catheter 10 is sealed to the penis 30. The catheter 10 can be removed from the penis 30 by pulling the upper portion 11a of the tubular sheath away from the penis 30 and down over the outer surface 14 toward the tube 17. This can be accomplished in any manner which accommodates the purpose and the comfort of the patient. It will be appreciated that one appropriate method of removing the catheter 10 would be to roll the upper portion 11a up again so that it returns generally to the same orientation as that shown in FIG. 1. When this method of removing the catheter 10 is used, the adhesive layer 15 will release the outer surface of the penis 30, and the catheter 10 can be removed with relative ease.

Although, as described hereinbelow, the tubular sheaths 11 can be made by combining two or more layers of a silicone rubber solution or of separate silicone rubber solutions, once the unvulcanized silicone rubber solutions are dried and cured in a vulcanizing process, the respective silicone rubber solution coatings will be combined to form a single unitary tubular sheath without separate layers. It will be appreciated that any silicone rubber solution used to form silicone rubber products of one type or another may be used to form the silicone rubber sheath of the present invention. The vulcanizing process may be either a heat process, a catalyzed process employing a catalyzing agent or agents, a combination of the two, or any other suitable vulcanizing process known in the art.

Referring now also to FIGS. 4–11, the preferred method of making an external urinary catheter 10 of the present invention includes a series of steps designed to coat a mandrel 20. The mandrel 20 has a generally cylindrical shape which narrows at its lower end 22. The lower end 22 includes a major conical portion 22a, an enlarged cylindrical portion 22b, a minor conical portion 22c and a narrowed cylindrical portion 22d. The surfaces will preferably be coated with Teflon ®, or the mandrel 20 is made of Teflon ®. In preferred embodiments a series of mandrels 20 are attached to a pallet 23 so that numerous external urinary catheters 10 can be mass produced. This is preferably accomplished by coating each of the mandrels 20 in a series of coating steps which are preferably accomplished by dipping each of the mandrels 20, preferably in unison, in a series of dip tanks 80a–f which are raised up to a precise level calculated to accomplish a specific task. It will be appreciated that a series (not shown) of pallets can also be employed so that a continuous mechanized production operation can be developed to mass produce catheters 10 in accordance with the present invention. The pallet 23 or a series of pallets (not shown) are advanced by a mechanized advancing system 88. It will be appreciated that any known mechanization system for advancing the pallet 23 or pallets can be used.

In a preferred embodiment of the present method, a mandrel 20 is first dipped into a first dip tank 80a containing a mandrel release agent 81, preferably a polydimethylsiloxane fluid (Dow Corning 360 Medical Fluid from Dow Corning, Inc., Midland, MI 48360 having a viscosity of 12,500 centistokes, diluted about 1:25 in hexamethyldisiloxane. In order to insure that a first portion 24 of the mandrel 20, which is an area on the surface of the mandrel 20 which lies between the lines designated A and B, is completely coated by the silicone fluid, the pallet 23 to which the mandrel 20 is attached is centered over the first dip tank 80a and the dip tank 80a is raised a distance which is calculated to dip the mandrel 20 into the silicone fluid so that the line designated A is fully submersed in the fluid and the entire first portion 24 of the mandrel 20 is coated with silicone fluid. The mandrel 20 is then lowered, the silicone coating 40 is given time to dry, and the pallet 23 is then advanced to a second dip tank 80b containing a fluid 82 containing an adhesive material. Although it will be appreciated that any adhesive material which will bond to unvulcanized silicone rubber during a vulcanizing process can be used in the present method, the preferred adhesive material is Monsanto 788 Acrylic Adhesive from Monsanto Corporation, St. Louis, MO. The second dip tank 80b is then raised a distance calculated to dip the mandrel 20 into the adhesive fluid 82 in the second dip tank 80b so that the entire first portion 24 of the mandrel 20 between the lines designated A and B is coated by the adhesive fluid 82 to form an adhesive coating 42 over the silicone coating 40. The dip tank 80b is then lowered and allowed to dry for a period of time.

The pallet 23 is then advanced to a third dip tank 80c containing a solvent 83, preferably trichloroethane (trichlor 1,1,1) or xylene, which will strip the adhesive coating 42 and the silicone fluid coating 40 from the mandrel 20. In this case, the dip tank 80c is raised a distance calculated to dip the mandrel 20 into the solvent 83 up to the line on the mandrel 20 designated B so that the adhesive coating 42 and the silicone fluid coating 40 which coat a second portion 26 of the mandrel 20 below the line designated B, and proximate the lower end 22 of the mandrel 20, will be stripped. In alternate embodiments, the tank 80c may be lowered and then raised again several times to assure rapid stripping action. The pallet can also be advanced to a new dip tank (not shown) having a second solvent (not shown) to further strip the second portion 26 of the mandrel 20. In preferred embodiments, however, a vibrator (not shown) is connected to the pallet 23 or the mandrel 20 to vibrate the mandrel 20 and speed the removal of the adhesive coating 42, or an ultrasonic cleaning system (not shown) is incorporated into the dip tank 80c.

After the cleaning step, the mandrel 20 is then advanced on the pallet 23 to a fourth dip tank 80d containing a silicone rubber solution 84 preferably having a siloxane solvent, most preferably a hexamethyldisiloxane solvent. The disiloxane solvent is preferred because it does not destroy the integrity of the adhesive strip 44 which remains on the first portion 24 of the mandrel 20 following the stripping step or steps previously mentioned. When the mandrel 20 is dipped into the silicone rubber solution 84 in the fourth dip tank 80d, the unvulcanized silicone rubber solution 84 coats the mandrel 20 and overcoats the silicone coating 40 and the adhesive strip 44 to form a first overcoat layer 46 of the silicone rubber solution. The fourth dip tank 80d is then lowered, the unvulcanized silicone rubber overcoat layer 46 is allowed to dry for a period of time, and the pallet 23 is advanced to a fifth dip tank 80e containing an additional silicone rubber solution 85, preferably having a greater concentration of silicone rubber. The solvent may also be varied. The dip tank 80e is then raised and mandrel 20 is dipped into the dip tank 80e to a level just below the line designated B so as to add an additional thickness 46a over the first overcoat layer 46 proximate the lower end 22 of the mandrel 20 to form a final overcoat layer 48. The dip tank 80e is then lowered and the final overcoat layer 48 is allowed to air dry so that the solvent in the silicone rubber overcoat layer 48 is allowed to evaporate. It will be appreciated that additional dip tanks may be provided for additional dipping steps.

In the preferred embodiment of the present method, the final silicone rubber solution overcoat layer 48 is then vulcanized or cured in an oven (not shown) at an elevated temperature, preferably about 205° F. It will be appreciated that the temperature is maintained at a level below the boiling point of the solvent or solvents used in the silicone rubber solution solutions which are used, so that the vulcanized silicone rubber which results will not have any bubbles caused by the evaporation or boiling off of the solvent. Furthermore, it will also be appreciated that other silicone rubber systems which are catalyzed without heat may also be used to provide a vulcanizing system which will result in a vulcanized silicone rubber elastomeric sheath 50 following the vulcanization of the final silicone rubber solution overcoat layer 48. During the vulcanizing process, any distinction between the initial silicone rubber solution overcoat layer 46 and the subsequent additional thickness 46a is eliminated during the vulcanizing process and a single unitary tubular sheath 50 is formed. Once the silicone rubber has been vulcanized, a tubular pre-catheter form 10' is formed. The pre-catheter form 10' is then allowed to cool and the silicone rubber sheath 50 is then rolled from the top 25 of the mandrel 20 so that an inner surface 12 of the pre-catheter form 10' is rolled up onto the outer surface 14 of the pre-catheter form 10' or elastomeric sheath 50. In the process of rolling the elastomeric sheath 50 up upon the outer surface 14 thereof, the adhesive strip 44 which has now been integrally bonded with the silicone rubber during the vulcanizing process, comes into contact with the outer surface 14 of the silicone rubber sheath 50. When the sheath 50 is rolled up, a portion of the silicone fluid coating 80 or mandrel release agent 40 will adhere to the adhesive strip 44. The silicone fluid which adheres to the adhesive strip is absorbed by the outer surface 14 of the silicone rubber sheath 11 when it comes into contact therewith in the pre-use orientation shown in FIG. 1.

It will be appreciated that it is important that the trace amounts of silicone fluid adhering to the adhesive strip 44 are absorbed by the outer surface 14, because if it were not absorbed it could interfere with the adherence of the adhesive layer 15 with the penis 30. It will also be appreciated that the silicone fluid is just one of many mandrel release agents which can be used to coat the mandrel, however. Other agents which prevent the adhesive material 44 from making it overly difficult to remove the pre-catheter form 10' from the mandrel can also be used. Siloxane fluids which allow for the easy removal of the pre-catheter form 10' from the mandrel are especially desirable so long as they are also absorbed by silicone rubber surfaces.

The adhesive strip 44 is selected for its ability to bond with the silicone rubber during the vulcanized process and for its lack of adherence when it comes into contact with vulcanized silicone rubber after the vulcanizing process. It will be appreciated that any biocompatible adhesive which will cross-link with silicone rubber during the vulcanizing process will be a suitable adhesive so long as it will releasably adhere to new silicone rubber surfaces with which it comes into contact after it is bonded to the inner surface of a silicone rubber sheath during the vulcanizing process.

Referring now also to FIG. 12, the pre-catheter form 10' is taken off the mandrel 20, and the enclosed tip 53 of the pre-catheter form 10' is cut off or otherwise removed from the distal end of the pre-catheter form 10' to form the external urinary catheter shown in FIG. 1. When the catheter 10 is fully rolled up into its pre-use orientation shown in FIG. 1, it includes a single tubular sheath 11 having a unitary construction made of silicone rubber with an adhesive layer 15 integrally bonded thereto and interposed between the inner surface 12 and the outer surface 14. The adhesive layer 15 is integrally bonded to the inner surface 12 as a result of cross-linking between constituents in the adhesive material 44 and constituents in the unvulcanized silicone rubber of the overcoat layer 46 during the vulcanizing process. It will not, however, irreversably adhere or bond to any of the vulcanized silicone rubber surfaces with which it comes into contact after the vulcanizing process. The adhesive layer 15 does contact the outer surface 14, but any adherence thereto is limited to releasable adherence.

Figure 13:
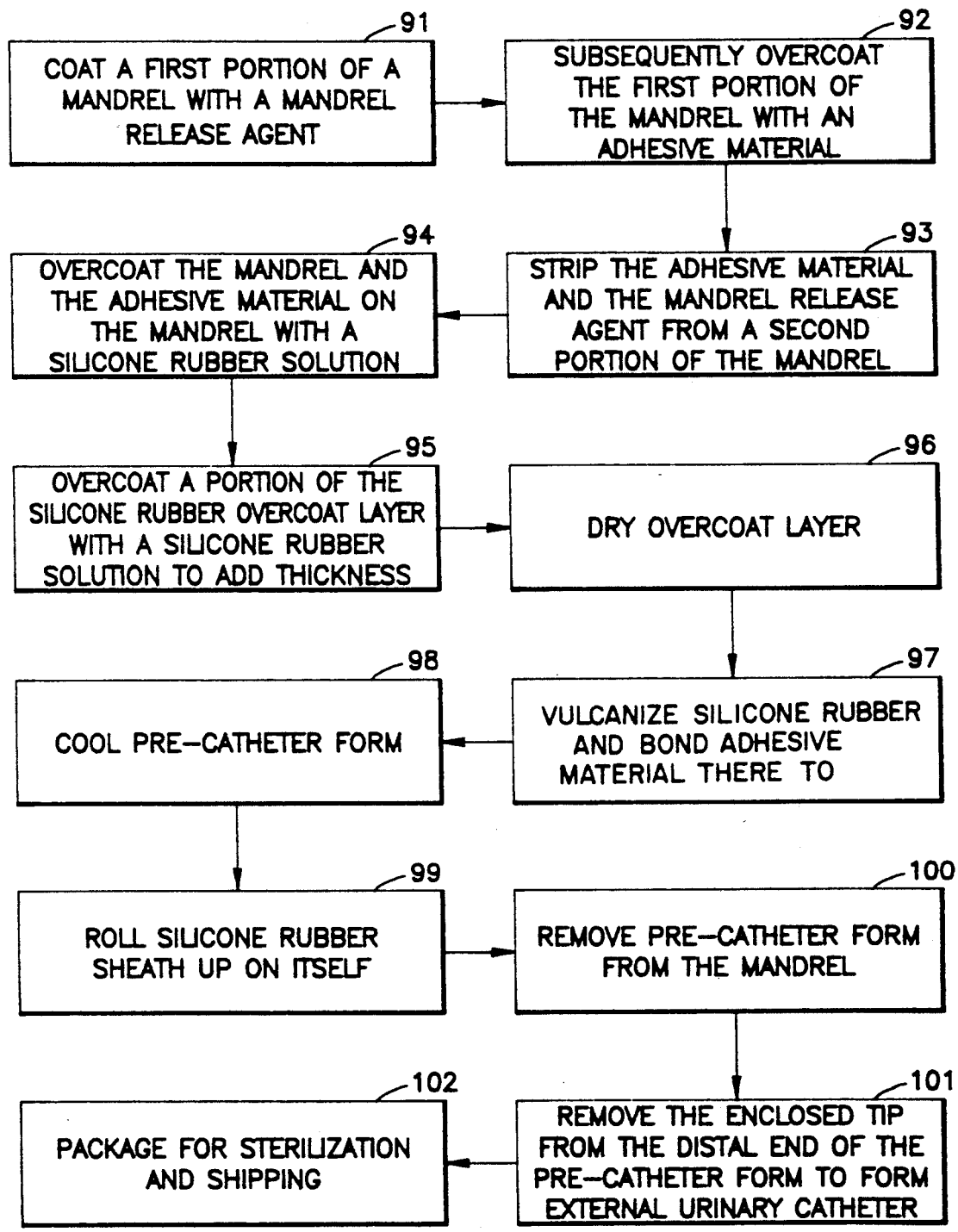
FIG. 13 is a flowchart describing the respective steps in a method of making external urinary catheters in accordance with the present invention.

Referring now also to FIG. 13, the steps of a method of making the external urinary catheter 10 of the present invention are disclosed. In a first step 91, a first portion 24 a mandrel 20 is coated with a mandrel release agent 81. In the second step 92, the first portion 24 of the mandrel 20 is subsequently overcoated with an adhesive material 82. In a third step 93, the coating of adhesive material 42 and the coating of mandrel release agent 40 are stripped from a second portion 26 of the mandrel 20. In a fourth step 94, the mandrel 20 and the remaining adhesive strip 44 on the mandrel 20 are overcoated with a first silicone rubber solution 84 to form an initial unvulcanized silicone rubber overcoat 46. In a fifth step 95, a portion of the silicone rubber overcoat layer 46 is overcoated with a second silicone rubber solution 85 to add thickness to the silicone rubber coating the lower portion 22 of the mandrel 20 and to form a final silicone rubber overcoat layer 48. In a sixth step 96, the final overcoat layer 48 is dried. In a seventh step 97, the final silicone rubber overcoat layer 48 is vulcanized and the adhesive strip 44 is bonded thereto. In an eighth step 98, the pre-catheter form 10', which is formed during the vulcanizing step 97, is cooled. In a ninth step 99, the silicone rubber sheath 50 is rolled up on itself so that the inner surface 12 comes into contact with the outer surface 14. In a tenth step 100, the pre-catheter form 10' is removed from the mandrel 20. In an eleventh step 101, the enclosed tip 53 is removed from the distal end of the pre-catheter form 10' to form the external urinary catheter 10 of the present invention. And in a twelfth step 102, the external urinary catheter 10 is packaged for subsequent sterilization and shipping in its pre-use orientation.

It is to be understood, however, that even though numerous characteristics and advantages of the present invention have been set forth in the foregoing description, together with details of the structure and function of the invention, the disclosure contained herein is illustrative, and changes in matters of order, shape, size and arrangement of parts and of steps may be made within the principles of the present invention and to the full extent indicated by the broad general meaning of the terms in which the appended claims are expressed.

What is claimed is:
1. An external urinary catheter, comprising:
(a) a tubular sheath having a construction made of silicone rubber, said silicone rubber sheath having an inner surface and an outer surface; and
(b) a layer of adhesive material directly and non-releasably bonded to a first portion of the inner surface; wherein the adhesive material can releasably contact portions of the outer surface such that the inner surface of said silicone rubber sheath can be rolled up upon the outer surface thereof so that the adhesive layer on the first portion of the inner surface comes into releasable contact with portions of the outer surface, and such that the adhesive material on the outer surface will then release any portions of the outer surface with which it has come into contact, while remaining bonded to the inner surface, when said silicone rubber sheath is forcibly unrolled.

2. The external urinary catheter of claim 1 wherein the first portion of the inner surface, to which the adhesive material is bonded, is a tubular, strip forming a continuous band, along the inner surface of said silicone rubber sheath.

3. The external urinary catheter of claim 1 wherein the adhesive material is a synthetic material which bonds to silicone rubber when in contact with unvulcanized rubber during a vulcanizing process such that the adhesive material cannot be readily peeled away from the inner surface.

4. The external urinary catheter of claim 3 wherein the adhesive material is an acrylic adhesive which can be bonded to silicone rubber during a vulcanizing process.

5. The external urinary catheter of claim 1 wherein the layer of adhesive material bonded to the inner surface of the silicone rubber sheath is at least partially coated with a silicone fluid mandrel release agent which is absorbed by the outer surface of the silicone rubber sheath when it comes into contact therewith such that the silicone fluid mandrel release agent is dispersed within and becomes part of the silicone rubber sheath proximate the outer surface.

6. The external urinary catheter of claim 1 wherein the inner surface of the silicone rubber sheath is rolled up upon the outer surface of the silicone rubber sheath for storage prior to use, and wherein the adhesive material bonded to the inner surface is in releasable contact with portions of the outer surface of the silicone rubber sheath.

7. An external urinary catheter comprising:
(a) a tubular sheath having a construction made of silicone rubber, said silicone rubber sheath having an inner surface and an outer surface; and
(b) a layer of adhesive material directly and non-releasably bonded to a first portion of the inner surface; wherein constituents within the adhesive material are cross-linked to constituents within the silicone rubber; and further wherein the inner surface of the silicone rubber sheath is rolled up on the outer surface thereof for storage of said external urinary catheter prior to use such that the adhesive material is in releasable contact with portions of the outer surface; wherein the adhesive material on the inner surface will release any portion of the outer surface with which it is in contact if said silicone rubber sheath is forcibly unrolled.

8. The external urinary catheter of claim 7 wherein the first portion of the inner surface, to which the adhesive material, is bonded, is a tubular strip forming a band along the inner surface of said silicone rubber sheath.

9. The external urinary catheter of claim 7 wherein the adhesive material is a synthetic material which bonds to silicone rubber when in contact with unvulcanized silicone rubber during a vulcanizing process.

10. The external urinary catheter of claim 9 wherein the adhesive material is an acrylic adhesive which can be bonded to silicone rubber during a vulcanizing process.

* * * * *